United States Patent
Ushio

(10) Patent No.: US 10,018,827 B2
(45) Date of Patent: Jul. 10, 2018

(54) OBJECTIVE OPTICAL SYSTEM FOR ENDOSCOPE

(71) Applicant: OLYMPUS CORPORATION, Hachioji-shi, Tokyo (JP)

(72) Inventor: Yasuaki Ushio, Hamura (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/678,791

(22) Filed: Aug. 16, 2017

(65) Prior Publication Data

US 2017/0343790 A1  Nov. 30, 2017

Related U.S. Application Data

(63) Continuation of application No. PCT/JP2016/066673, filed on Jun. 3, 2016.

(30) Foreign Application Priority Data

Jun. 18, 2015  (JP) .................. 2015-123031

(51) Int. Cl.
*G02B 23/24* (2006.01)
*G02B 9/58* (2006.01)
(Continued)

(52) U.S. Cl.
CPC ........ *G02B 23/243* (2013.01); *A61B 1/00163* (2013.01); *G02B 9/34* (2013.01); *G02B 9/58* (2013.01)

(58) Field of Classification Search
CPC .......... G02B 23/243; G02B 9/58; G02B 9/60; G02B 9/62; G02B 9/64; G02B 23/2438; G02B 9/34; G02B 13/04; A61B 1/00163
See application file for complete search history.

(56) References Cited

U.S. PATENT DOCUMENTS

2009/0237807 A1  9/2009  Sasamoto
2011/0235192 A1*  9/2011  Uzawa ............... A61B 1/00096
                                                     359/785
(Continued)

FOREIGN PATENT DOCUMENTS

JP    4695662 B2    6/2011
JP    4997348 B2    8/2012
(Continued)

OTHER PUBLICATIONS

International Search Report (ISR) and Written Opinion dated Sep. 6, 2016 issued in International Application No. PCT/JP2016/066673.

(Continued)

*Primary Examiner* — Jordan Schwartz
(74) *Attorney, Agent, or Firm* — Holtz, Holtz & Volek PC

(57) ABSTRACT

An objective optical system for endoscope includes, in order from an object side, a front lens group having a negative refractive power as a whole, an aperture stop, and a rear lens group having a positive refractive power as a whole. The front lens group includes, in order from the object side, a single first lens having a negative refractive power and a single second lens having a positive refractive power. The rear lens group includes a single third lens having a positive refractive power, and a cemented lens of a fourth lens having a positive refractive power and a fifth lens having a negative refractive power. An object-side surface of the first lens is a flat surface, the second lens has a meniscus shape having a convex surface directed toward an image side, and the third lens has a biconvex shape.

8 Claims, 9 Drawing Sheets

(51) Int. Cl.
  *G02B 9/34* (2006.01)
  *A61B 1/00* (2006.01)

(56) References Cited

U.S. PATENT DOCUMENTS

| | | | |
|---|---|---|---|
| 2012/0057251 A1 | 3/2012 | Takato | |
| 2012/0147164 A1 | 6/2012 | Sasamoto | |
| 2012/0224268 A1 | 9/2012 | Takato | |
| 2013/0163092 A1 | 6/2013 | Morita | |
| 2013/0163094 A1* | 6/2013 | Takada | G02B 15/14 359/684 |
| 2014/0092225 A1 | 4/2014 | Sasamoto | |
| 2015/0268460 A1* | 9/2015 | Takada | G02B 13/04 359/738 |
| 2016/0238832 A1 | 8/2016 | Sasamoto | |
| 2016/0282591 A1* | 9/2016 | Mizusawa | A61B 1/00 |
| 2016/0306162 A1 | 10/2016 | Ushio | |

FOREIGN PATENT DOCUMENTS

| | | |
|---|---|---|
| JP | 2013003267 A | 1/2013 |
| WO | 2011070930 A1 | 6/2011 |
| WO | 2011145505 A1 | 11/2011 |
| WO | 2012008312 A1 | 1/2012 |
| WO | 2013002019 A1 | 1/2013 |
| WO | 2013042456 A1 | 3/2013 |
| WO | 2015064614 A1 | 5/2015 |
| WO | 2016031586 A1 | 3/2016 |

OTHER PUBLICATIONS

International Preliminary Report on Patentability (IPRP) dated Dec. 28, 2017 issued in counterpart International application No. PCT/JP2016/066873.

* cited by examiner

OBJECTIVE OPTICAL SYSTEM FOR ENDOSCOPE

CROSS-REFERENCE TO RELATED APPLICATION

The present application is a continuation application of PCT/JP2016/066673 filed on Jun. 3, 2016 which is based upon and claims the benefit of priority from the Japanese Patent Application No. 2015-123031 filed on Jun. 18, 2015; the entire contents of which are incorporated herein by reference.

BACKGROUND OF THE INVENTION

Field of the Invention

The present invention relates to an objective optical system for endoscope which is small-sized and is to be used in an endoscope with a bright and highly-defined image quality.

Description of the Related Art

In recent years, for improving diagnosis, high quality of images picked up by endoscope is achieved. With achievement of high-quality images and small-sizing of image pickup elements such as a CCD (charge coupled device) and a CMOS (complementary metal-oxide semiconductor) for endoscope, a pixel pitch of the image pickup element is becoming small year by year. With this, an objective optical system for endoscope is required to satisfy optical performance such as widening of angel of view and correction of aberration, while being small-sized. As objective optical systems for endoscope, optical systems proposed in Japanese Patent No. 4695662 publication and Japanese Patent No. 4997348 Publication are available.

The present invention provides the following means.

An objective optical system for endoscope includes in order from an object side:

a front lens group having a negative refractive power as a whole;

an aperture stop; and a rear lens group having a positive refractive power as a whole, wherein the front lens group includes in order from the object side, a first lens which is a single lens having a negative refractive power and a second lens which is a single lens having a positive refractive power, and the rear lens group includes a third lens which is a single lens having a positive refractive power and a cemented lens of a fourth lens having a positive refractive power and a fifth lens having a negative refractive power, and an object-side surface of the first lens is a flat surface, and the second lens has a meniscus shape having a convex surface directed toward an image side, and the third lens has a biconvex shape, and the objective optical system for endoscope satisfies the following conditional expressions (1) and (2)

$$-2.0 \leq f_1/\text{Ih} \leq -1.39 \quad (1)$$

$$-0.2 \leq SF_3 \leq 0.61 \quad (2)$$

where, $f_1$ denotes a focal length of the first lens,

Ih denotes the maximum image height of the objective optical system for endoscope, and $SF_3$ denotes a shape factor which is expressed by $SF_3 = (R_{3L}+R_{3R})/(R_{3L}-R_{3R})$, when a radius of curvature of an object-side surface of the third lens is let to be $R_{3L}$ and a radius of curvature of an image-side surface of the third lens is lens to be $R_{3R}$.

DETAILED DESCRIPTION OF THE INVENTION

Reasons for and effects of adopting such arrangement for an objective optical system for endoscope according to an embodiment will be described below by referring to the accompanying diagrams. However, the present invention is not restricted to the following embodiment.

Figure 1:
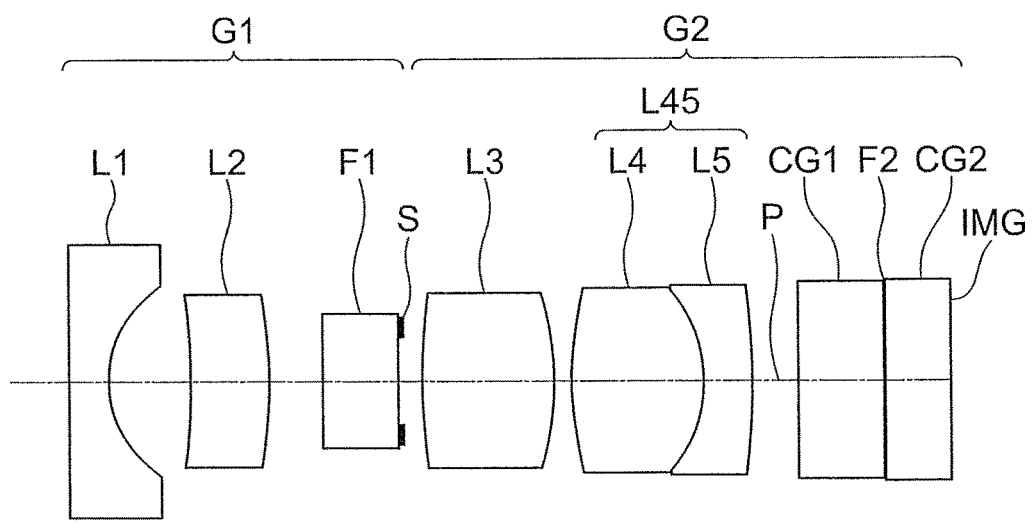
FIG. 1 is a diagram showing a cross-sectional view of an arrangement of an objective optical system for endoscope according to an embodiment of the present invention.

FIG. 1 is a cross-sectional view of the arrangement of the objective optical system for endoscope according to the present embodiment.

The objective optical system for endoscope according to the present embodiment, includes in order from an object side, a front lens group G1 having a negative refractive power as a whole, an aperture stop S, and a rear lens group G2 having a positive refractive power as a whole, wherein the front lens group G1 includes in order from the object side, a first lens L1 which is a single lens having a negative refractive power and a second lens L2 which is a single lens having a positive refractive power, and the rear lens group G2 includes a third lens L3 which is a single lens having a positive refractive power and a cemented lens L45 of a fourth lens L4 having a positive refractive power and a fifth lens L5 having a negative refractive power, and an object-side surface of the first lens L1 is a flat surface, and the second lens L2 has a meniscus shape having a convex surface directed toward an image side, and the third lens L3 has a biconvex shape, and the objective optical system for endoscope satisfies the following conditional expression (1).

$$-2.0 \leq f_1/\text{Ih} \leq -1.39 \quad (1)$$

where, $f_1$ denotes a focal length of the first lens L1, and

Ih denotes the maximum image height of the objective optical system for endoscope.

Firstly, for arranging an objective optical system having a small-size and a favorable optical performance which can be used in an endoscope, the first lens L1 having a negative refractive power is disposed nearest to object. Accordingly, it is made possible to adopt a retro-focus type arrangement as the arrangement of the objective optical system.

Moreover, it is preferable to make the following arrangement for the first lens L1. When a dirt or blood is adhered to a lens surface on the object side of the first lens L1 during the observation by endoscope, cleansing of the lens surface is carried out by jetting water from a nozzle provided at a front end of the endoscope. At the time of cleansing, when a shape of the lens surface of the object side of the first lens L1 is a convex shaped, the dirt is not removed easily. Moreover, when the shape of the lens surface on the object side of the first lens L1 is a concave shape, the water removal becomes unfavorable due to accumulation of water. Furthermore, when the lens surface of the object side of the first lens L1 is a convex surface, it is susceptible to be scratched or cracked due to an impact.

Therefore, the first lens L1 having a negative refractive power is let to be a lens having planoconcave shape, the first lens L1 having a negative refractive power is disposed such that a flat surface is directed toward the object side. By making such arrangement, the water removal at the time of observation is made favorable and cracking of lens due to an impact is reduced.

Moreover, the second lens L2 having a positive refractive power and a meniscus shape is disposed such that the convex surface is directed toward the image side. By making such arrangement, it is possible to converge a light beam such that a lens diameter does not become large, while correcting an aberration that occurs in the first lens L1 having a negative refractive power.

The aperture stop S and a lens group having a positive refractive power of the third lens L3 having a positive refractive power and having a biconvex shape and the fourth lens L4 having a positive refractive power and having a biconvex shape are disposed on the image side of the second lens L2 having a meniscus shape. The third lens L3 and the fourth lens L4 contribute mainly to image formation. Furthermore, dividing the positive refractive power between the third lens L3 having a positive refractive power and biconvex shape and the fourth lens L4 having a positive refractive power and biconvex shape, even when an F-number is made fast, it is possible to suppress the occurrence of aberration and to distribute the refractive power necessary for small-sizing.

Moreover, the cemented lens L45 of the fourth lens L4 having a positive refractive power and biconvex shape and the fifth lens L5 having a negative refractive power is disposed at a position at which a height of a marginal ray on the image side of the third lens L3 becomes high. A chromatic aberration is corrected by the cemented lens L45.

In such arrangement, for shortening the overall length while making the arrangement of retro-focus type, the first lens L1 having a negative refractive power is required to have a comparatively strong negative refractive power. When the negative refractive power of the first lens L1 is made excessively strong, an amount of aberration that occurs becomes excessively large. For instance, mainly a coma aberration and a chromatic aberration of magnification are not corrected thoroughly at the second lens L2 having a positive refractive power, and a spherical aberration is not corrected thoroughly at the third lens L3 having a positive refractive power and the fourth lens L4 having a positive refractive power, and an optical performance is degraded. Consequently, a favorable optical performance cannot be achieved, and degradation of optical performance due to a manufacturing variation becomes large. Therefore, by setting appropriately the negative refractive power of the first lens L1, the optical system has a fast F-number, and it is possible to achieve both of the favorable optical performance and small-sizing.

For such reason, in the objective optical system for endoscope according to the present embodiment, it is desirable to satisfy the following conditional expression (1).

$$-2.0 \leq f_1/\text{Ih} \leq -1.39 \quad (1)$$

where, $f_1$ denotes a focal length of the first lens L1, and

Ih denotes the maximum image height of the objective optical system for endoscope.

When an upper limit value of conditional expression (1) is exceeded, the negative refractive power becomes excessively strong. Accordingly, the spherical aberration, the coma aberration, and the chromatic aberration occur and the performance is degraded, and an image quality is susceptible to be degraded due to the manufacturing variation.

When a value falls below a lower limit value of conditional expression (1), the negative refractive power becomes excessively weak. Accordingly, the overall length and a lens diameter of the objective optical system for endoscope become large, and the small-sizing cannot be carried out.

It is more desirable to satisfy the following conditional expression (1') instead of conditional expression (1).

$$-1.8 \leq f_1/\text{Ih} \leq -1.39 \tag{1'}$$

Furthermore, it is even more desirable to satisfy the following conditional expression (1") instead of conditional expression (1).

$$-1.6 \leq f_1/\text{Ih} \leq -1.4 \tag{1"}$$

The third lens L3 having a positive refractive power has a comparatively strong refractive power for making the retro-focus arrangement. Consequently, an amount of aberration that occurs is also large. Therefore, in the objective optical system for endoscope according to the present embodiment, it is desirable to satisfy the following conditional expression (2).

$$-0.2 \leq SF_3 \leq 0.61 \tag{2}$$

where, $SF_3$ denotes a shape factor which is expressed by $SF_3 = (R_{3L}+R_{3R})/(R_{3L}-R_{3R})$, when a radius of curvature of an object-side surface of the third lens L3 is let to be $R_{3L}$ and a radius of curvature of an image-side surface of the third lens L3 is lens to be $R_{3R}$.

When an upper limit value of conditional expression (2) is exceeded, the radius of curvature of the object side of the third lens L3 becomes excessively large, and particularly the spherical aberration cannot be corrected, thereby leading to degradation of the optical performance.

When a value falls below a lower limit value of conditional expression (2), since a principal point moves to the object side, the overall length becomes large.

It is more desirable to satisfy the following conditional expression (2') instead of conditional expression (2).

$$0.2 \leq SF_3 \leq 0.61 \tag{2'}$$

Furthermore, it is even more desirable to satisfy the following conditional expression (2") instead of conditional expression (2).

$$0.3 \leq SF_3 \leq 0.5 \tag{2"}$$

Moreover, for the third lens L3 having a positive refractive power and the fourth lens L4 having a positive refractive power, a light ray height is lowered at the fourth lens L4 for a center beam and the light ray height rises at the fourth lens L4 for a marginal beam. Therefore, to keep a balance of the spherical aberration and the coma aberration, in the objective optical system for endoscope according to the present embodiment, it is desirable to satisfy the following conditional expression (3).

$$-0.27 \leq SF_{34} \leq 0.37 \tag{3}$$

where, $SF_{34}$ denotes a shape factor which is expressed by $SF_{34} = (R_{3R}+R_{4L})/(R_{3R}-R_{4L})$, when a radius of curvature of an image-side surface of the third lens L3 is let to be $R_{3R}$ and a radius of curvature of an object-side surface of the fourth lens L4 is let to be $R_{4L}$.

When an upper limit value of conditional expression (3) is exceeded, a marginal performance is degraded due to the coma aberration in particular.

When a value falls below a lower limit value of conditional expression (3), the spherical aberration is degraded, and an aberration of the overall image field is degraded.

It is more desirable to satisfy the following conditional expression (3') instead of conditional expression (3).

$$-0.2 \leq SF_{34} \leq 0.25 \tag{3'}$$

Furthermore, it is even more desirable to satisfy the following conditional expression (3") instead of conditional expression (3).

$$-0.17 \leq SF_{34} \leq 0.15 \tag{3"}$$

Moreover, in the objective optical system for endoscope according to the present embodiment, it is desirable that the first lens L1 having a negative refractive power and the fifth lens L5 having a negative refractive power satisfy the following conditional expression (4) in order to keep balance of the overall optical length and correction of the astigmatism in particular, in the periphery of image field.

$$0.15 \leq (1/\text{Fno}) \times (f_1/f_5) \leq 0.3 \tag{4}$$

where,

Fno denotes an effective F-number of the objective optical system for endoscope, $f_1$ denotes the focal length of the first lens L1, and $f_5$ denotes the focal length of the fifth lens L5.

When an upper limit value of conditional expression (4) is exceeded, the refractive power of the first lens L1 becomes excessively weak, and either small-sizing becomes difficult or the refractive power of the fifth lens L5 becomes excessively strong and the astigmatism is corrected excessively, thereby leading to degradation of performance.

When a value falls below a lower limit value of conditional expression (4), either the refractive power of the first lens L1 becomes excessively strong or the refractive power of the fifth lens L5 becomes excessively weak, and the astigmatism cannot be corrected favorably, thereby making it difficult to achieve a favorable image quality. Moreover, it becomes an objective optical system having a slow F-number.

It is more desirable to satisfy the following conditional expression (4') instead of conditional expression (4).

$$0.17 \leq (1/\text{Fno}) \times (f_1/f_5) \leq 0.27 \tag{4'}$$

Furthermore, it is even more desirable to satisfy the following conditional expression (4") instead of conditional expression (4).

$$0.2 \leq (1/\text{Fno}) \times (f_1/f_5) \leq 0.26 \tag{4"}$$

Moreover, both the second lens L2 and the third lens L3 have a positive refractive power. Also, the second lens L2 and the third lens L3 are disposed to sandwich the aperture stop S in between. Therefore, it is an arrangement to cancel an aberration in the periphery of image field. However, with this arrangement, an aberration is not corrected adequately. Therefore, an arrangement of the fifth lens L5 having a negative refractive power at a position at which the height of the marginal light ray becomes high becomes significant.

Therefore, in the objective optical system for endoscope according to the present embodiment, it is desirable to satisfy the following conditional expression (5).

$$-2.0 \leq f_{23}/f_5 \leq -1.0 \quad (5)$$

where, $f_{23}$ denotes a combined focal length of the second lens L2 and the third lens L3, and $f_5$ denotes a focal length of the fifth lens L5.

When an upper limit value of conditional expression (5) is exceeded, either the refractive power of the second lens L2 and the refractive power of the third lens L3 become excessively strong and an aberration at a center and at the periphery of the image field is deteriorated, or the refractive power of the fifth lens L5 becomes excessively weak and an aberration at the periphery of the image field is not corrected adequately.

When a value falls below a lower limit value of conditional expression (5), either the refractive power of the second lens L2 and the refractive power of the third lens L3 become excessively weak and the overall length becomes large, or the refractive power of the fifth lens L5 becomes excessively strong and the chromatic aberration of magnification, the astigmatism, and an aberration at the periphery of the image field are corrected excessively.

It is more desirable to satisfy the following conditional expression (5') instead of conditional expression (5).

$$-1.5 \leq f_{23}/f_5 \leq -1.15 \quad (5')$$

Furthermore, it is even more desirable to satisfy the following conditional expression (5") instead of conditional expression (5).

$$-1.4 \leq f_{23}/f_5 \leq -1.1 \quad (5'')$$

The first lens L1 having a negative refractive power and the fourth lens L4 having a positive refractive power have an arrangement that bears a main function of retro-focus. Therefore, the first lens L1 having a negative refractive power and the fourth lens L4 having a positive refractive power are related to the overall optical length. Furthermore, the first lens L1 having a negative refractive power and the fourth lens L4 having a positive refractive power being away from the aperture stop S, are also related to the optical performance in the periphery of the image field. Therefore in the objective optical system for endoscope according to the present embodiment, it is desirable to satisfy the following conditional expression (6).

$$-1.1 \leq f_1/f_4 \leq -0.7 \quad (6)$$

where, $f_1$ denotes the focal length of the first lens, and
$f_4$ denotes the focal length of the fourth lens.

When an upper limit value of conditional expression (6) is exceeded, either the refractive power of the first lens L1 becomes weak and the overall length becomes large, or the refractive power of the fourth lens L4 becomes excessively strong and correction of the coma aberration becomes difficult.

When a value falls below a lower limit value of conditional expression (6), since the refractive power of the first lens L1 becomes strong, the image quality is susceptible to be degraded due to the manufacturing variation or since the refractive power of the fourth lens L4 becomes weak, the overall length becomes large.

It is more desirable to satisfy the following conditional expression (6') instead of conditional expression (6).

$$-1.0 \leq f_1/f_4 \leq 0.7 \quad (6')$$

Furthermore, it is even more desirable to satisfy the following conditional expression (6") instead of conditional expression (6).

$$-0.8 \leq f_1/f_4 \leq -0.7 \quad (6'')$$

Both the first lens L1 and the fourth lens L4 have a comparatively strong refractive power. Consequently, the first lens L1 and the fourth lens L4 have an effect on a curvature of field. Therefore, in the objective optical system for endoscope according to the present embodiment, it is desirable to satisfy the following conditional expression (7).

$$0.25 \leq R_{1R}/R_{4L} \leq 0.7 \quad (7)$$

where, $R_{1R}$ denotes a radius of curvature of an image-side surface of the first lens, and $R_{4L}$ denotes a radius of curvature of an object-side surface of the fourth lens.

When an upper limit value of conditional expression (7) is exceeded, the refractive power of the first lens L1 becomes excessively strong, and the image quality is susceptible to be degraded due to the manufacturing variation.

When a value falls below a lower limit value of conditional expression (7), the symmetry of the first lens L1 and the fourth lens L4 is degraded, and Petzval sum becomes large, as a result of which various aberrations cannot be corrected favorably.

It is more desirable to satisfy the following conditional expression (7') instead of conditional expression (7).

$$0.25 \leq R_{1R}/R_{4L} \leq 0.45 \quad (7')$$

Furthermore, it is even more desirable to satisfy the following conditional expression (7") instead of conditional expression (7).

$$0.3 \leq R_{1R}/R_{4L} \leq 0.4 \quad (7'')$$

The first lens L1 and the fifth lens L5 are disposed far away from the aperture stop S. Consequently, since the optical performance in the periphery of the image field is affected and the height of the marginal light ray becomes high, the lens diameter is also affected. Therefore, in the objective optical system for endoscope according to the present embodiment, it is desirable to satisfy the following conditional expression (8).

$$-0.3 \leq R_{1R}/R_{5R} \leq 0 \quad (8)$$

where, $R_{1R}$ denotes a radius of curvature of an image-side surface of the first lens, and $R_{5R}$ denotes a radius of curvature of an image-side surface of the fifth lens.

When an upper limit value of conditional expression (8) is exceeded, an angle of incidence of a light ray on an image pickup element becomes large, an attenuation of light occurs in a peripheral portion, and the back focus becomes short leading to a deterioration of assemblability.

When a value falls below a lower limit value of conditional expression (8), either the radius of curvature of the first lens L1 becomes large and the lens diameter becomes excessively large or the radius of curvature of the fifth lens L5 becomes excessively large and an aberration, particularly, the astigmatism and the coma aberration, in the periphery of the image field are deteriorated.

It is more desirable to satisfy the following conditional expression (8') instead of conditional expression (8).

$$-0.21 \leq R_{1R}/R_{5R} \leq 0 \quad (8')$$

Furthermore, it is even more desirable to satisfy the following conditional expression (8″) instead of conditional expression (8).

$$-0.1351 \leq R_{1R}/R_{5R} \leq 0 \qquad (8'')$$

At the time of in-vivo screening, for reducing a possibility of overlooking a site of lesion, it is desirable to have a wide angle of view. Particularly, a half angle of view of at least 62° is necessary. Therefore, in the objective optical system for endoscope according to the present embodiment, it is desirable to satisfy the following conditional expression (9).

$$\omega \geq 62° \qquad (9)$$

where,

ω denotes a half angle of view of the objective optical system for endoscope.

When a value falls below a lower limit value of conditional expression (9), an observation range is narrowed, and at the time of in-vivo screening, there is a possibility of overlooking a site of lesion.

It is more desirable to satisfy the following conditional expression (9′) instead of conditional expression (9).

$$\omega \geq 65° \qquad (9')$$

Example 1

An objective optical system for endoscope according to an example 1 of the present invention will be described below.

Figure 2A:
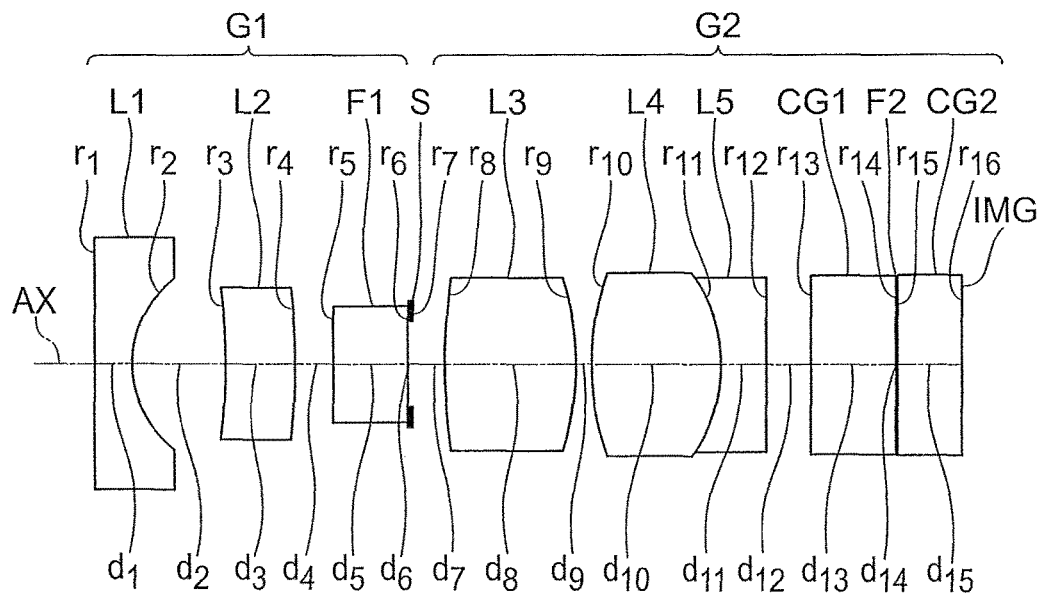
FIG. 2A is a cross-sectional view showing an arrangement of an objective optical system for endoscope according to an example 1 of the present invention.
Figures 2B, 2C, 2D, 2E:
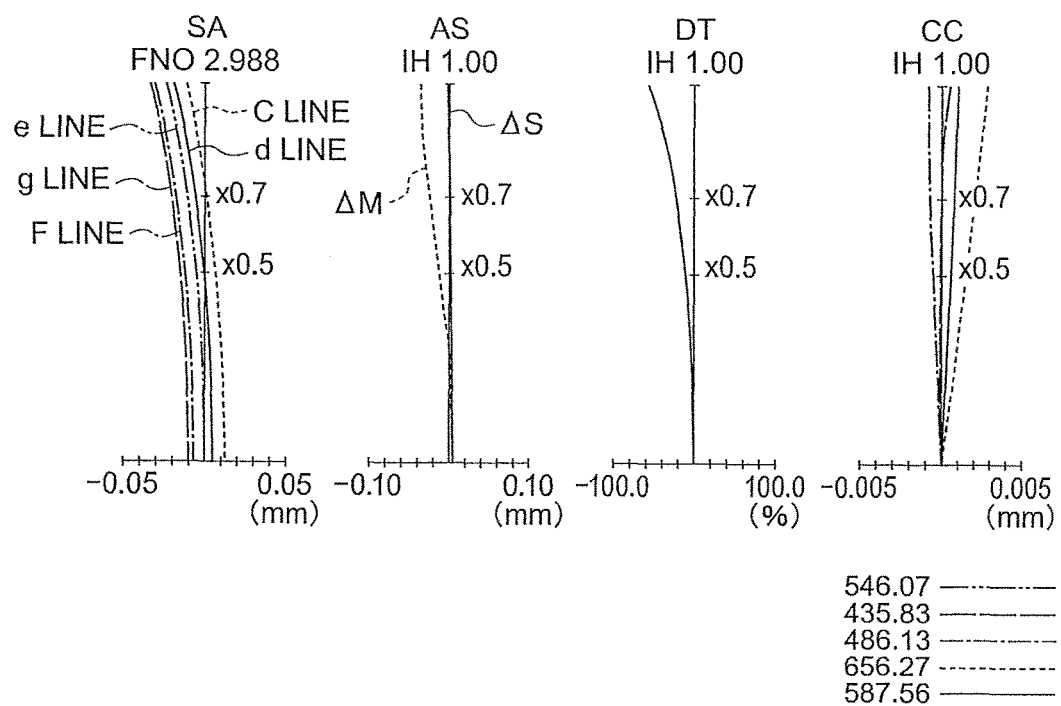
FIG. 2B, FIG. 2C, FIG. 2D, and FIG. 2E are aberration diagrams showing a spherical aberration (SA), an astigmatism (AS), a distortion (DT), and a chromatic aberration of magnification (CC) for the objective optical system for endoscope according the example 1.

FIG. 2A is a cross-sectional view of the objective optical system for endoscope according to the present example, FIG. 2B shows a spherical aberration (SA), FIG. 2C shows an astigmatism (AS), FIG. 2D shows a distortion (DT), and FIG. 2E shows a chromatic aberration of magnification (CC) for the objective optical system for endoscope according to the present example.

In the present example, the objective optical system for endoscope includes in order from an object side, a first lens L1 having a negative refractive power and having a planoconcave shape with a flat surface directed toward the object side, a second meniscus lens L2 having a positive refractive power and having a convex surface directed toward an image side, an infra-red absorbing filter F1, an aperture stop S, a third lens L3 having a positive refractive power and having a biconvex shape, a fourth lens L4 having a positive refractive power and having a biconvex shape, a fifth meniscus lens L5 having a negative refractive power and having a convex surface directed toward the image side, a cover glass CG1, and an image pickup element cover glass CG2. Here, the fourth lens L4 having a positive refractive power and the fifth meniscus lens L5 having a negative refractive power are cemented. The cover glass CG1 and the image pickup element cover glass CG2 are cemented via a cemented layer F2. Moreover, in all the examples below, IMG denotes an image pickup surface.

Example 2

An objective optical system for endoscope according to an example 2 of the present invention will be described below.

Figure 3A:
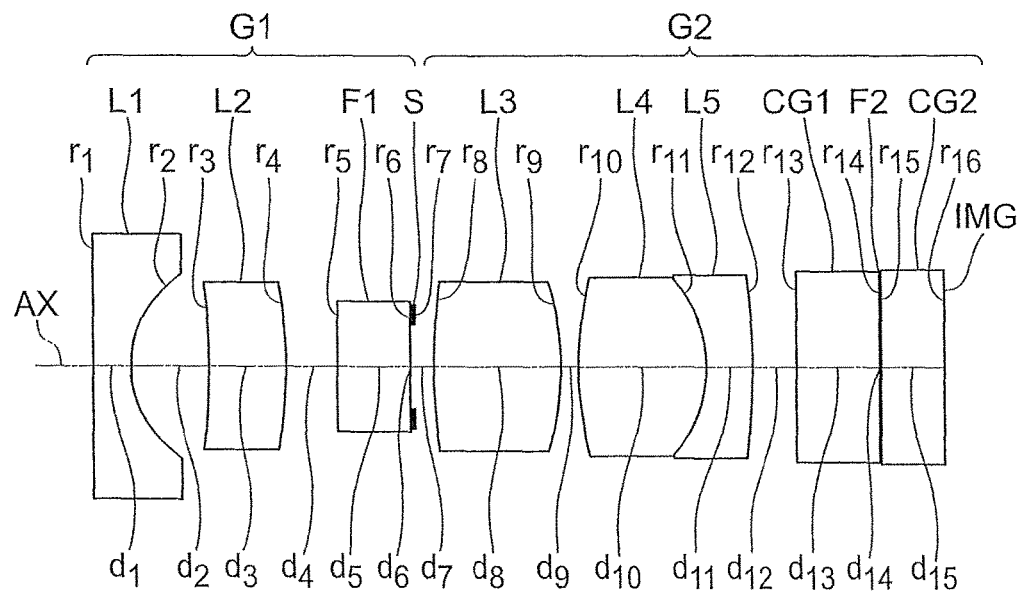
FIG. 3A is a cross-sectional view showing an arrangement of an objective optical system for endoscope according to an example 2 of the present invention.
Figures 3B, 3C, 3D, 3E:
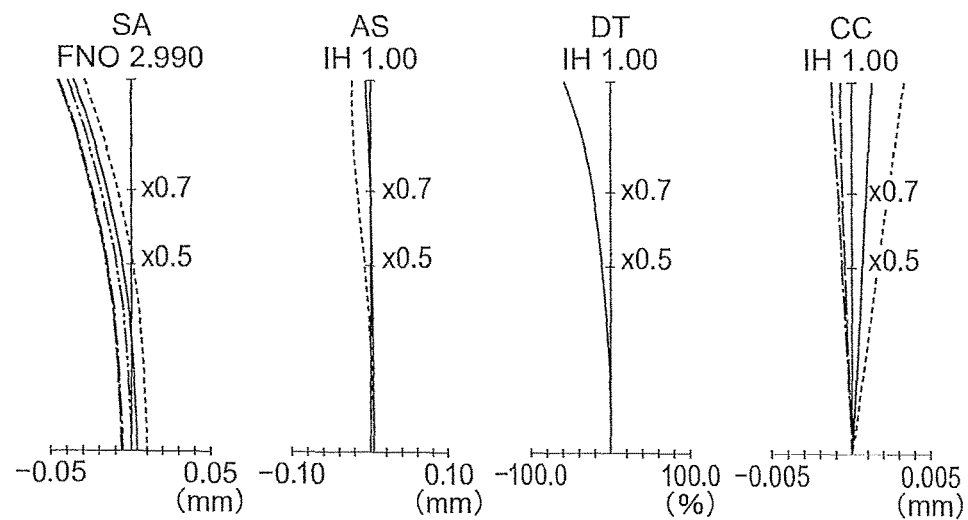
FIG. 3B, FIG. 3C, FIG. 3D, and FIG. 3E are aberration diagrams showing a spherical aberration (SA), an astigmatism (AS), a distortion (DT), and a chromatic aberration of magnification (CC) for the objective optical system for endoscope according to the example 2.

FIG. 3A is a cross-sectional view of the objective optical system for endoscope according to the present example, FIG. 3B shows a spherical aberration (SA), FIG. 3C shows an astigmatism (AS), FIG. 3D shows a distortion (DT), and FIG. 3E shows a chromatic aberration of magnification (CC) for the objective optical system for endoscope according to the present example.

In the present example, the objective optical system for endoscope includes in order from an object side, a first lens L1 having a negative refractive power and having a planoconcave shape with a flat surface directed toward the object side, a second meniscus lens L2 having a positive refractive power and having a convex surface directed toward an image side, an infra-red absorbing filter F1, an aperture stop S, a third lens L3 having a positive refractive power and having a biconvex shape, a fourth lens L4 having a positive refractive power and having a biconvex shape, a fifth meniscus lens L5 having a negative refractive power and having a convex surface directed toward the image side, a cover glass CG1, and an image pickup element cover glass CG2. Here, the fourth lens L4 having a positive refractive power and the fifth meniscus lens L5 having a negative refractive power are cemented. The cover glass CG1 and the image pickup element cover glass CG2 are cemented via a cemented layer F2.

Example 3

An objective optical system for endoscope according to an example 3 of the present invention will be described below.

Figure 4A:
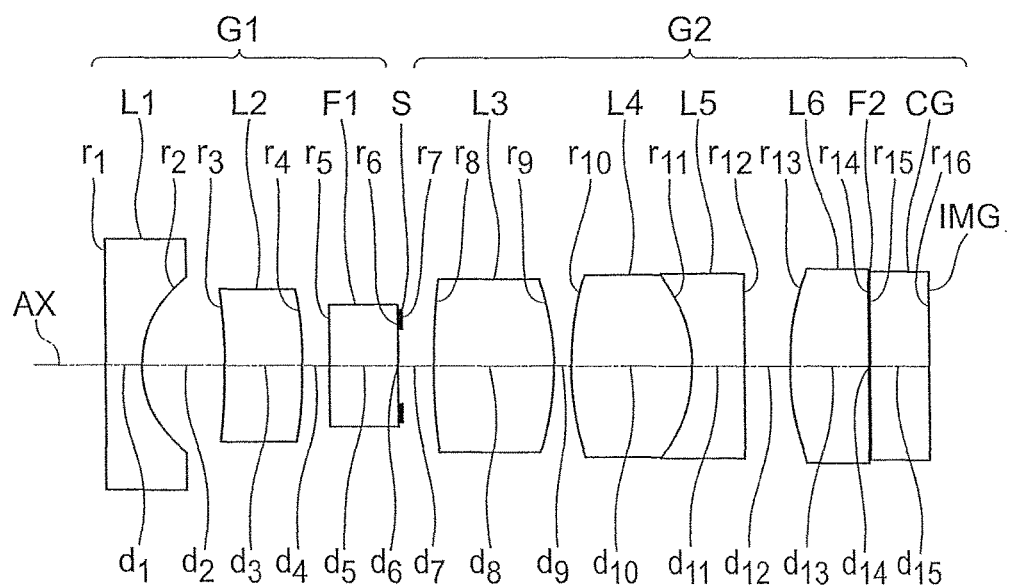
FIG. 4A is a cross-sectional view showing an arrangement of an objective optical system for endoscope according to an example 3 of the present invention.
Figures 4B, 4C, 4D, 4E:
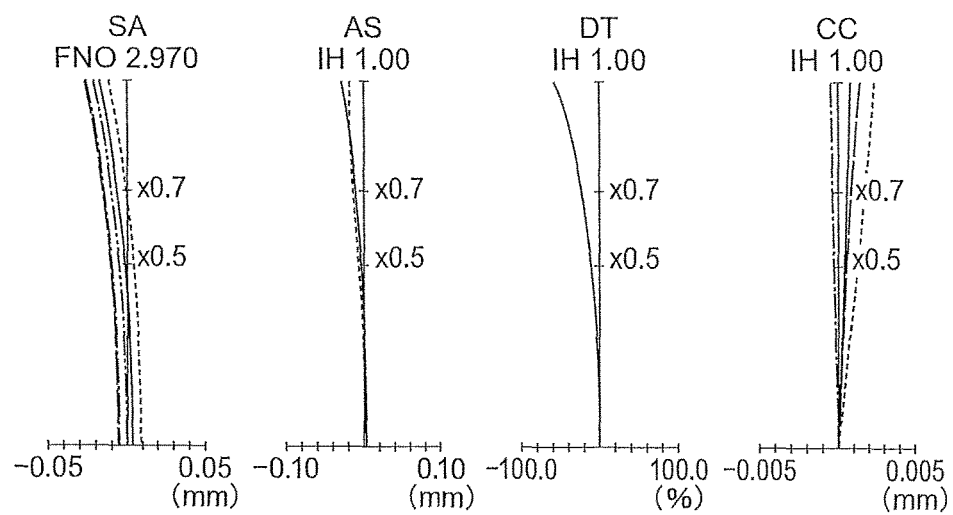
FIG. 4B, FIG. 4C, FIG. 4D, and FIG. 4E are aberration diagrams showing a spherical aberration (SA), an astigmatism (AS), a distortion (DT), and a chromatic aberration of magnification (CC) for the objective optical system for endoscope according to the example 3.

FIG. 4A is a cross-sectional view of the objective optical system for endoscope according to the present example, FIG. 4B shows a spherical aberration (SA), FIG. 4C shows an astigmatism (AS), FIG. 4D shows a distortion (DT), and FIG. 4E shows a chromatic aberration of magnification (CC) for the objective optical system for endoscope according to the present example.

In the present example, the objective optical system for endoscope includes in order from an object side, a first lens L1 having a negative refractive power and having a planoconcave shape with a flat surface directed toward the object side, a second meniscus lens L2 having a positive refractive power and having a convex surface directed toward an image side, an infra-red absorbing filter F1, an aperture stop S, a third lens L3 having a positive refractive power and having a biconvex shape, a fourth lens L4 having a positive refractive power and having a biconvex shape, a fifth meniscus lens L5 having a negative refractive power and having a planoconcave shape with a flat surface directed toward the image side, a cover glass L6 having a planoconvex shape with a convex surface directed toward the object side, and an image pickup element cover glass CG. Here, the fourth lens L4 having a positive refractive power and the fifth lens L5 having a negative refractive power are cemented. The cover glass L6 and the image pickup element cover glass CG are cemented via a cemented layer F2.

Example 4

An objective optical system for endoscope according to an example 4 of the present invention will be described below.

Figure 5A:
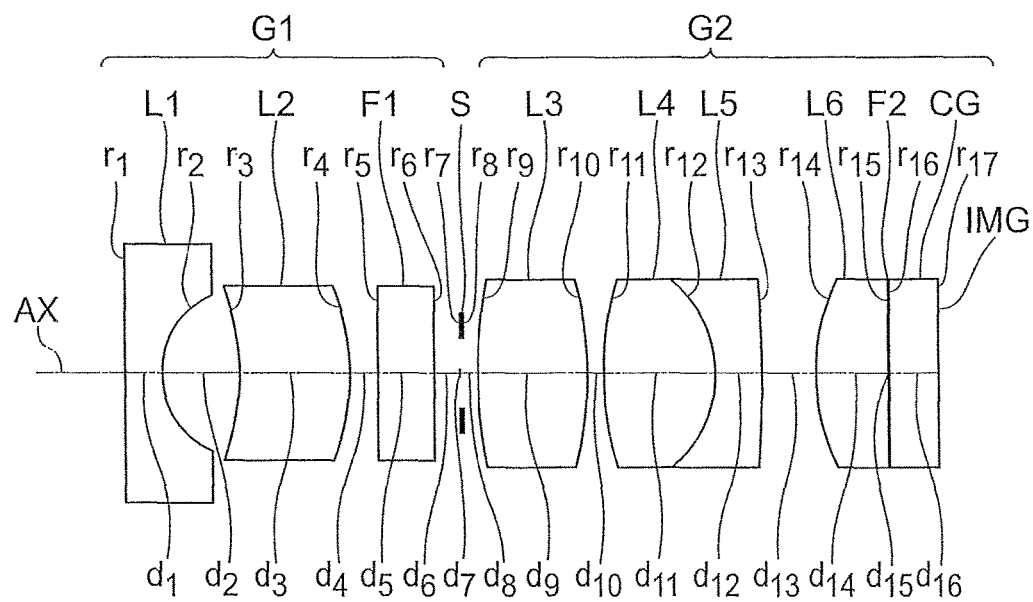
FIG. 5A is a cross-sectional view showing an arrangement of an objective optical system for endoscope according to an example 4 of the present invention.
Figures 5B, 5C, 5D, 5E:
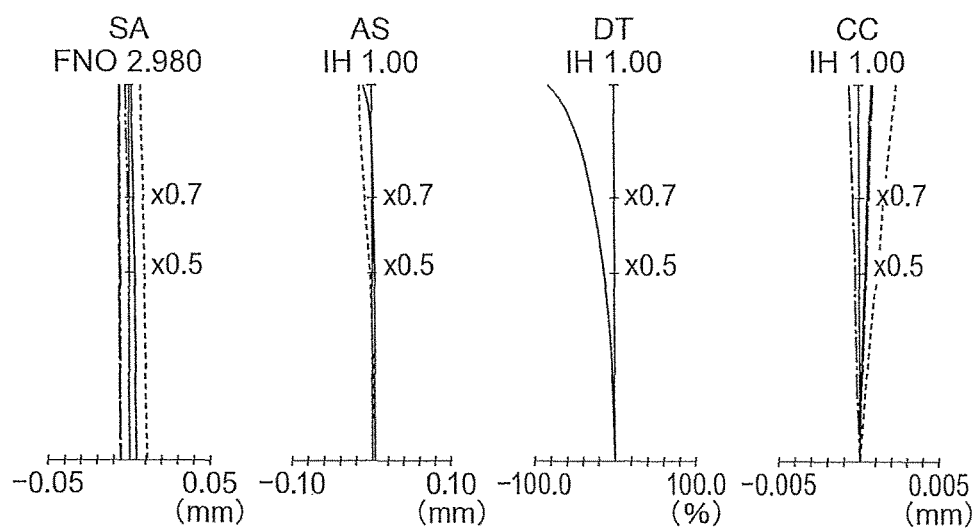
FIG. 5B, FIG. 5C, FIG. 5D, and FIG. 5E are aberration diagrams showing a spherical aberration (SA), an astigmatism (AS), a distortion (DT), and a chromatic aberration of magnification (CC) for the objective optical system for endoscope according to the example 4.

FIG. 5A is a cross-sectional view of the objective optical system for endoscope according to the present example, FIG. 5B shows a spherical aberration (SA), FIG. 5C shows an astigmatism (AS), FIG. 5D shows a distortion (DT), and FIG. 5E shows a chromatic aberration of magnification (CC) for the objective optical system for endoscope according to the present example.

In the present example, the objective optical system for endoscope includes in order from an object side, a first lens L1 having a negative refractive power and having a planoconcave shape with a flat surface directed toward the object side, a second meniscus lens L2 having a positive refractive power and having a convex surface directed toward an image side, an infra-red absorbing filter F1, an aperture stop S, a third lens L3 having a positive refractive power and having a biconvex shape, a fourth lens L4 having a positive refractive power and having a biconvex shape, a fifth meniscus lens L5 having a negative refractive power and having a convex surface directed toward the image side, a cover glass L6 having a planoconvex shape with a convex surface directed toward the object side, and an image pickup element cover glass CG. Here, the fourth lens L4 having a positive refractive power and the fifth meniscus lens L5 having a negative refractive power are cemented. The cover glass L6 and the image pickup element cover glass CG are cemented via a cemented layer F2.

Example 5

An objective optical system for endoscope according to an example 5 of the present invention will be described below.

Figure 6A:
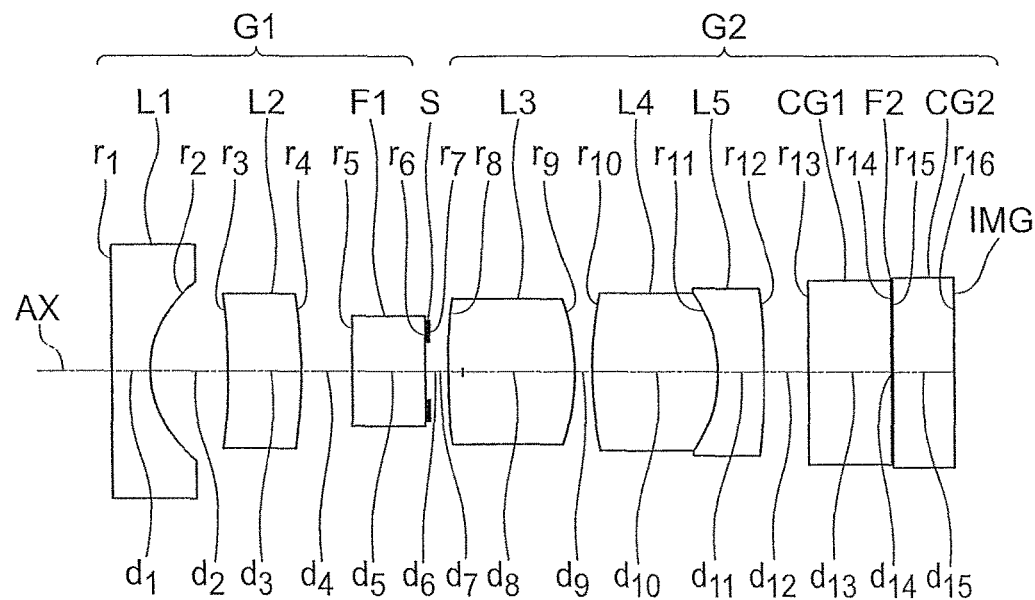
FIG. 6A is a cross-sectional view showing an arrangement of an objective optical system for endoscope according to an example 5 of the present invention.
Figures 6B, 6C, 6D, 6E:
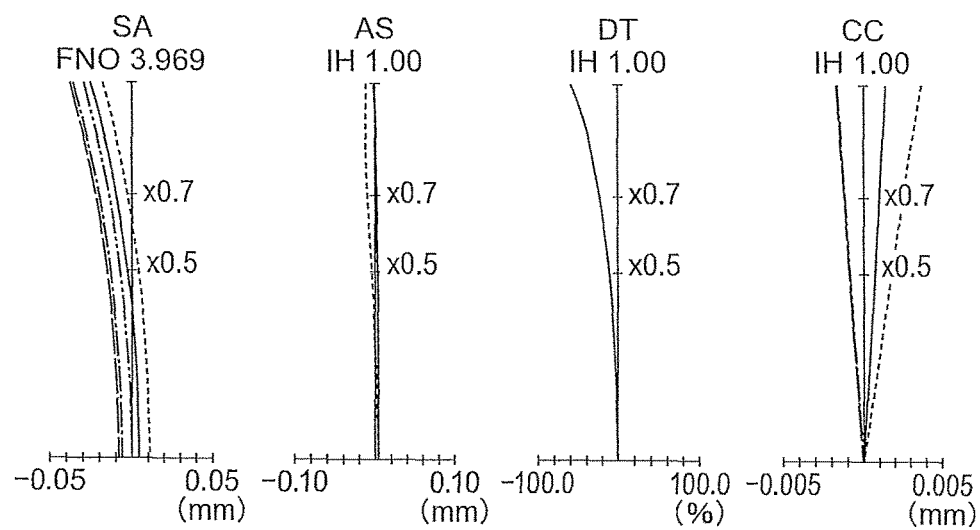
FIG. 6B, FIG. 6C, FIG. 6D, and FIG. 6E are aberration diagrams showing a spherical aberration (SA), an astigmatism (AS), a distortion (DT), and a chromatic aberration of magnification (CC) for the objective optical system for endoscope according to the example 5.

FIG. 6A is a cross-sectional view of the objective optical system for endoscope according to the present example, FIG. 6B shows a spherical aberration (SA), FIG. 6C shows an astigmatism (AS), FIG. 6D shows a distortion (DT), and FIG. 6E shows a chromatic aberration of magnification (CC) for the objective optical system for endoscope according to the present example.

In the present example, the objective optical system for endoscope includes in order from an object side, a first lens L1 having a negative refractive power and having a planoconcave shape with a flat surface directed toward the object side, a second meniscus lens L2 having a positive refractive power and having a convex surface directed toward an image side, an infra-red absorbing filter F1, an aperture stop S, a third lens L3 having a positive refractive power and having a biconvex shape, a fourth lens L4 having a positive refractive power and having a biconvex shape, a fifth meniscus lens L5 having a negative refractive power and having a convex surface directed toward the image side, a cover glass CG1, and an image pickup element cover glass CG2. Here, the fourth lens L4 having a positive refractive power and the fifth meniscus lens L5 having a negative refractive power are cemented. The cover glass CG1 and the image pickup element cover glass CG2 are cemented via a cemented layer F2.

Example 6

An objective optical system for endoscope according to an example 6 of the present invention will be described below.

Figure 7A:
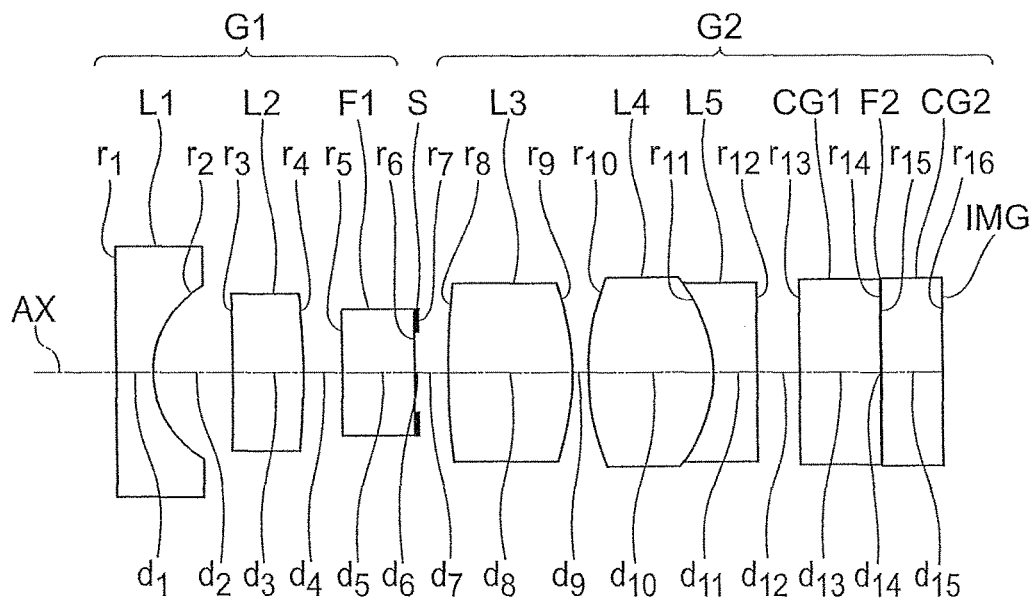
FIG. 7A is a cross-sectional view showing an arrangement of an objective optical system for endoscope according to an example 6 of the present invention.
Figures 7B, 7C, 7D, 7E:
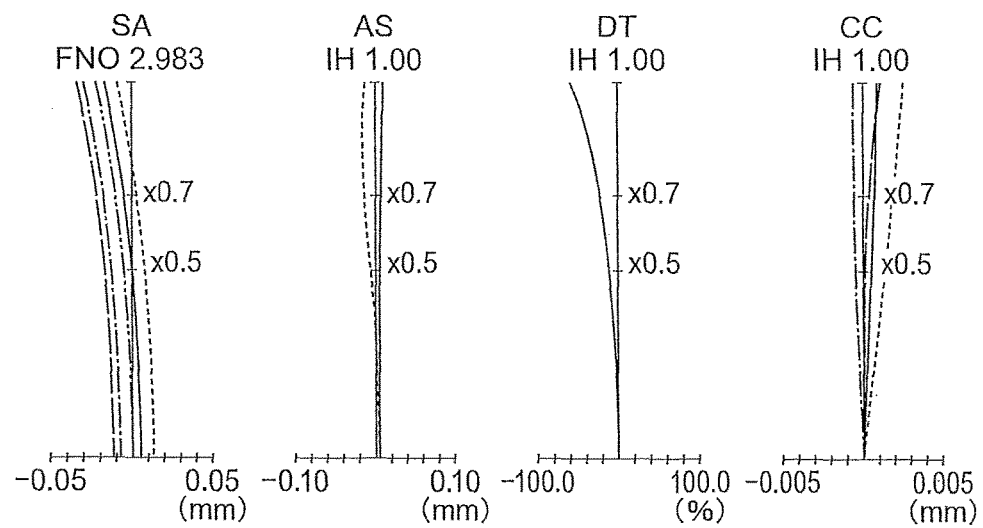
FIG. 7B, FIG. 7C, FIG. 7D, and FIG. 7E are aberration diagrams showing a spherical aberration (SA), an astigmatism (AS), a distortion (DT), and a chromatic aberration of magnification (CC) for the objective optical system for endoscope according to the example 6.

FIG. 7A is a cross-sectional view of the objective optical system for endoscope according to the present example, FIG. 7B shows a spherical aberration (SA), FIG. 7C shows an astigmatism (AS), FIG. 7D shows a distortion (DT), and FIG. 7E shows a chromatic aberration of magnification (CC) for the objective optical system for endoscope according to the present example.

In the present example, the objective optical system for endoscope includes in order from an object side, a first lens L1 having a negative refractive power and having a planoconcave shape with a flat surface directed toward the object side, a second meniscus lens L2 having a positive refractive power and having a convex surface directed toward an image side, an infra-red absorbing filter F1, an aperture stop S, a third lens L3 having a positive refractive power and having a biconvex shape, a fourth lens L4 having a positive refractive power and having a biconvex shape, a fifth lens L5 having a negative refractive power and having a planoconcave shape with a flat surface directed toward the image side, a cover glass CG1, and an image pickup element cover glass CG2. Here, the fourth lens L4 having a positive refractive power and the fifth lens L5 having a negative refractive power are cemented. The cover glass CG1 and the image pickup element cover glass CG2 are cemented via a cemented layer F2, Example 7

An objective optical system for endoscope according to an example 7 of the present invention will be described below.

Figure 8A:
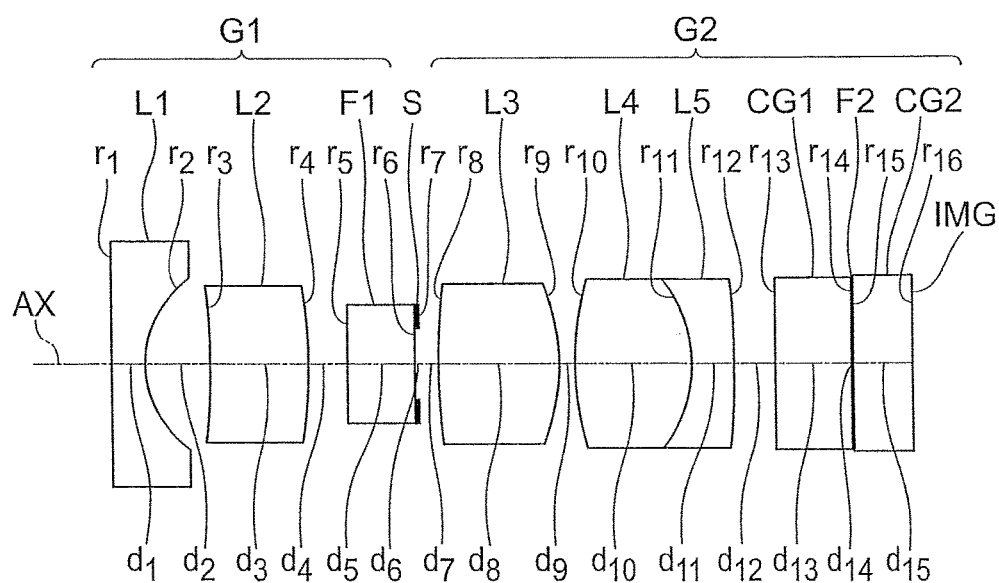
FIG. 8A is a cross-sectional view showing an arrangement of an objective optical system for endoscope according to an example 7 of the present invention.
Figures 8B, 8C, 8D, 8E:
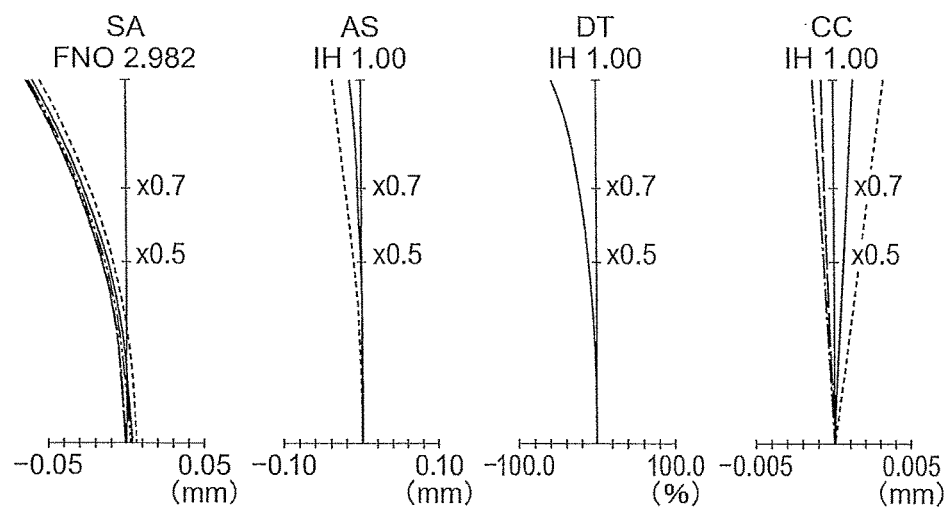
FIG. 8B, FIG. 8C, FIG. 8D, and FIG. 8E are aberration diagrams showing a spherical aberration (SA), an astigmatism (AS), a distortion (DT), and a chromatic aberration of magnification (CC) for the objective optical system for endoscope according to the example 7.

FIG. 8A is a cross-sectional view of the objective optical system for endoscope according to the present example, FIG. 8B shows a spherical aberration (SA), FIG. 8C shows an astigmatism (AS), FIG. 8D shows a distortion (DT), and FIG. 8E shows a chromatic aberration of magnification (CC) for the objective optical system for endoscope according to the present example.

In the present example, the objective optical system for endoscope includes in order from an object side, a first lens L1 having a negative refractive power and having a planoconcave shape with a flat surface directed toward the object side, a second meniscus lens L2 having a positive refractive power and having a convex surface directed toward an image side, an infra-red absorbing filter F1, an aperture stop S, a third lens L3 having a positive refractive power and having a biconvex shape, a fourth lens L4 having a positive refractive power and having a biconvex shape, a fifth meniscus lens L5 having a negative refractive power and having a convex surface directed toward the image side, a cover glass CG1, and an image pickup element cover glass CG2. Here, the fourth lens L4 having a positive refractive power and the fifth meniscus lens L5 having a negative refractive power are cemented. The cover glass CG1 and the image pickup element cover glass CG2 are cemented via a cemented layer F2.

Example 8

An objective optical system for endoscope according to an example 8 of the present invention will be described below.

Figure 9A:
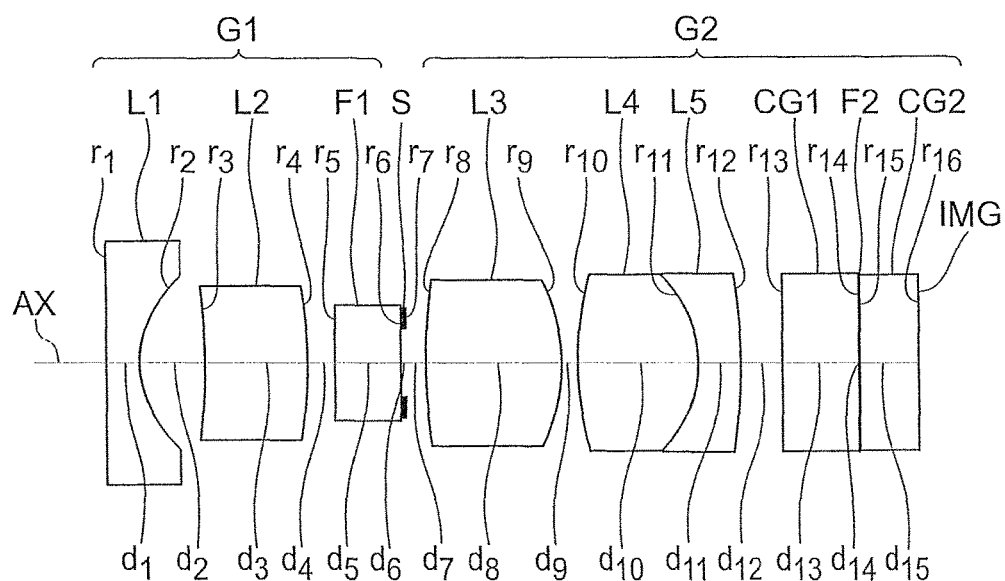
FIG. 9A is a cross-sectional view showing an arrangement of an objective optical system for endoscope according to an example 8 of the present invention.
Figures 9B, 9C, 9D, 9E:
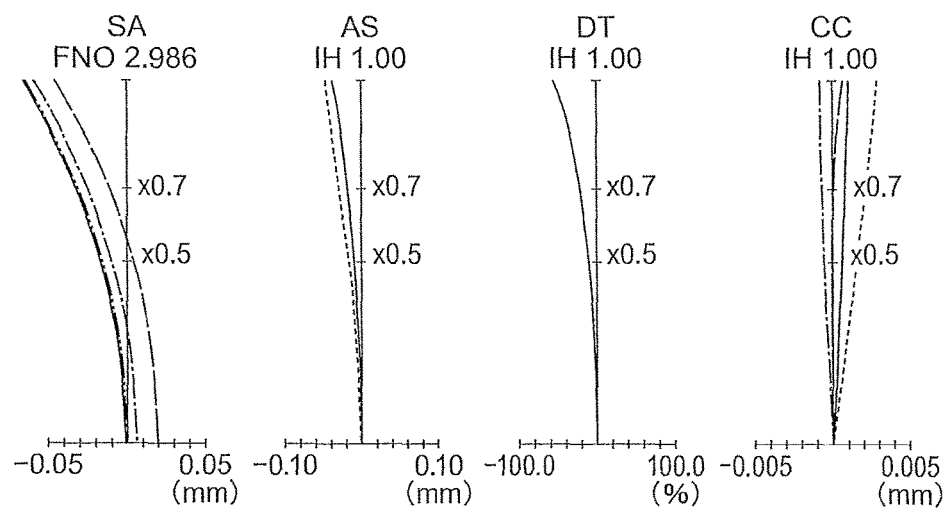
FIG. 9B, FIG. 9C, FIG. 9D, and FIG. 9E are aberration diagrams showing a spherical aberration (SA), an astigmatism (AS), a distortion (DT), and a chromatic aberration of magnification (CC) for the objective optical system for endoscope according to the example 8.

FIG. 9A is a cross-sectional view of the objective optical system for endoscope according to the present example, FIG. 9B shows a spherical aberration (SA), FIG. 9C shows an astigmatism (AS), FIG. 9D shows a distortion (DT), and FIG. 9E shows a chromatic aberration of magnification (CC) for the objective optical system for endoscope according to the present example.

In the present example, the objective optical system for endoscope includes in order from an object side, a first lens L1 having a negative refractive power and having a planoconcave shape with a flat surface directed toward the object side, a second meniscus lens L2 having a positive refractive power and having a convex surface directed toward an image side, an infra-red absorbing filter F1, an aperture stop S, a third lens L3 having a positive refractive power and having a biconvex shape, a fourth lens L4 having a positive refractive power and having a biconvex shape, a fifth meniscus lens L5 having a negative refractive power and having a convex surface directed toward the image side, a cover glass CG1, and an image pickup element cover glass CG2. Here, the fourth lens L4 having a positive refractive power and the fifth meniscus lens L5 having a negative refractive power are cemented. The cover glass CG1 and the image pickup element cover glass CG2 are cemented via a cemented layer F2.

Numerical data for each example is shown below. Regarding symbols, r denotes a radius of curvature of each lens surface, d denotes a distance between two lens surfaces, ne denotes a refractive index for an e-line of each lens, νd denotes Abbe's number for each lens, Fno denotes an F-number, ω denotes a half angle of view, and IH denotes an image height.

Example 1

| Unit mm | | | | |
|---|---|---|---|---|
| Surface data | | | | |
| Surface no. | r | d | ne | νd |
| Object plane | ∞ | 26.7261 | | |
| 1 | ∞ | 0.4439 | 1.88815 | 40.76 |
| 2 | 1.3000 | 1.0621 | | |
| 3 | −43.1176 | 0.8840 | 1.93429 | 18.90 |
| 4 | −9.5914 | 0.4677 | | |
| 5 | ∞ | 0.8909 | 1.51500 | 75.00 |
| 6 (Stop) | ∞ | 0.0668 | | |
| 7 | ∞ | 0.3915 | | |
| 8 | 8.8676 | 1.5506 | 1.88815 | 40.76 |
| 9 | −3.5574 | 0.1831 | | |
| 10 | 3.1503 | 1.5486 | 1.69979 | 55.53 |
| 11 | −1.8961 | 0.5488 | 1.93429 | 18.90 |
| 12 | ∞ | 0.5248 | | |
| 13 | ∞ | 1.0022 | 1.51825 | 64.14 |
| 14 | ∞ | 0.0223 | 1.51500 | 64.00 |
| 15 | ∞ | 0.7795 | 1.50700 | 63.26 |
| 16 (Image pickup surface) | | | | |

| Various data | |
|---|---|
| f | 1.059 |
| Fno. | 3.012 |
| ω | 66.9 |
| IH | 1.000 |
| LTL | 10.37 |

Example 2

| Unit mm | | | | |
|---|---|---|---|---|
| Surface data | | | | |
| Surface no. | r | d | ne | νd |
| Object plane | ∞ | 26.7261 | | |
| 1 | ∞ | 0.4466 | 1.88815 | 40.76 |
| 2 | 1.3245 | 0.9464 | | |
| 3 | −8.9062 | 0.9327 | 1.93429 | 18.90 |
| 4 | −6.2362 | 0.6283 | | |
| 5 | ∞ | 0.8909 | 1.51500 | 75.00 |
| 6 (Stop) | ∞ | 0.0668 | | |
| 7 | ∞ | 0.2171 | | |
| 8 | 7.0888 | 1.5554 | 1.88815 | 40.76 |
| 9 | −3.4775 | 0.2079 | | |
| 10 | 4.0958 | 1.5551 | 1.69979 | 55.53 |
| 11 | −1.6245 | 0.5567 | 1.93429 | 18.90 |
| 12 | −9.8112 | 0.5444 | | |
| 13 | ∞ | 1.0022 | 1.51825 | 64.14 |
| 14 | ∞ | 0.0223 | 1.51500 | 64.00 |
| 15 | ∞ | 0.7795 | 1.50700 | 63.26 |
| 16 (Image pickup surface) | | | | |

| Various data | |
|---|---|
| f | 1.041 |
| Fno. | 3.012 |
| ω | 67.4 |
| IH | 1.000 |
| LTL | 10.35 |

Example 3

| Unit mm | | | | |
|---|---|---|---|---|
| Surface data | | | | |
| Surface no. | r | d | ne | νd |
| Object plane | ∞ | 26.7261 | | |
| 1 | ∞ | 0.4454 | 1.88815 | 40.76 |
| 2 | 1.3675 | 1.0690 | | |
| 3 | −10.2962 | 1.0022 | 1.93429 | 18.90 |
| 4 | −5.6258 | 0.3341 | | |
| 5 | ∞ | 0.8909 | 1.49557 | 75.00 |
| 6 (Stop) | ∞ | 0.0668 | | |
| 7 | ∞ | 0.4009 | | |
| 8 | 9.4766 | 1.5590 | 1.88815 | 40.76 |
| 9 | −3.5835 | 0.2227 | | |
| 10 | 3.9243 | 1.5590 | 1.69979 | 55.53 |
| 11 | −1.9065 | 0.6682 | 1.93429 | 18.90 |
| 12 | ∞ | 0.5805 | | |
| 13 | 3.6020 | 1.0022 | 1.51825 | 64.14 |
| 14 | ∞ | 0.0223 | 1.51500 | 64.00 |
| 15 | ∞ | 0.7795 | 1.50700 | 63.26 |
| 16 (Image pickup surface) | | | | |

| Various data | |
|---|---|
| f | 1.048 |
| Fno. | 2.983 |
| ω | 66.6 |
| IH | 1.000 |
| LTL | 10.60 |

Example 4

| Unit mm | | | | |
|---|---|---|---|---|
| Surface data | | | | |
| Surface no. | r | d | ne | νd |
| Object plane | ∞ | 21.6783 | | |
| 1 | ∞ | 0.5828 | 1.88815 | 40.76 |
| 2 | 1.3800 | 1.2587 | | |
| 3 | −3.9557 | 1.8182 | 1.85504 | 23.78 |
| 4 | −3.6853 | 0.4429 | | |
| 5 | ∞ | 0.9324 | 1.49557 | 75.00 |
| 6 | ∞ | 0.4196 | | |
| 7 (Stop) | ∞ | 0.0699 | | |
| 8 | ∞ | 0.2331 | | |
| 9 | 8.3963 | 1.7716 | 1.83932 | 37.16 |
| 10 | −5.4522 | 0.2564 | | |

-continued

| Unit mm | | | | |
|---|---|---|---|---|
| 11 | 5.2308 | 1.8182 | 1.73234 | 54.68 |
| 12 | −1.9580 | 0.7459 | 1.93429 | 18.90 |
| 13 | −22.1492 | 0.8872 | | |
| 14 | 3.4739 | 1.1655 | 1.51825 | 64.14 |
| 15 | ∞ | 0.0233 | 1.51500 | 64.00 |
| 16 | ∞ | 0.8159 | 1.50700 | 63.26 |
| 17 (Image pickup surface) | | | | |

| Various data | |
|---|---|
| f | 0.968 |
| Fno. | 2.989 |
| ω | 81.1 |
| IH | 1.000 |
| LTL | 13.24 |

Example 5

| Unit mm | | | | |
|---|---|---|---|---|
| Surface data | | | | |
| Surface no. | r | d | ne | νd |
| Object plane | ∞ | 26.7261 | | |
| 1 | ∞ | 0.4537 | 1.88815 | 40.76 |
| 2 | 1.3405 | 0.9553 | | |
| 3 | −8.9042 | 0.9083 | 1.93429 | 18.90 |
| 4 | −6.2408 | 0.6337 | | |
| 5 | ∞ | 0.8909 | 1.51500 | 75.00 |
| 6 (Stop) | ∞ | 0.0668 | | |
| 7 | ∞ | 0.2178 | | |
| 8 | 8.3852 | 1.5546 | 1.88815 | 40.76 |
| 9 | −3.1907 | 0.2108 | | |
| 10 | 4.2329 | 1.5549 | 1.69979 | 55.53 |
| 11 | −1.6823 | 0.5571 | 1.93429 | 18.90 |
| 12 | −10.8415 | 0.5477 | | |
| 13 | ∞ | 1.0022 | 1.51825 | 64.14 |
| 14 | ∞ | 0.0223 | 1.51500 | 64.00 |
| 15 | ∞ | 0.7795 | 1.50700 | 63.26 |
| 16 (Image pickup surface) | | | | |

| Various data | |
|---|---|
| f | 1.038 |
| Fno. | 3.999 |
| ω | 65.9 |
| IH | 1.000 |
| LTL | 10.36 |

Example 6

| Unit mm | | | | |
|---|---|---|---|---|
| Surface data | | | | |
| Surface no. | r | d | ne | νd |
| Object plane | ∞ | 26.7261 | | |
| 1 | ∞ | 0.4476 | 1.88815 | 40.76 |
| 2 | 1.2417 | 1.0018 | | |
| 3 | −37.2536 | 0.8877 | 1.93429 | 18.90 |
| 4 | −8.4509 | 0.4826 | | |
| 5 | ∞ | 0.8909 | 1.51500 | 75.00 |
| 6 (Stop) | ∞ | 0.0668 | | |
| 7 | ∞ | 0.3743 | | |
| 8 | 8.8789 | 1.5557 | 1.88815 | 40.76 |
| 9 | −3.5618 | 0.2045 | | |

-continued

| Unit mm | | | | |
|---|---|---|---|---|
| 10 | 3.1440 | 1.5487 | 1.69979 | 55.53 |
| 11 | −1.8948 | 0.5543 | 1.93429 | 18.90 |
| 12 | ∞ | 0.5333 | | |
| 13 | ∞ | 1.0022 | 1.51825 | 64.14 |
| 14 | ∞ | 0.0223 | 1.51500 | 64.00 |
| 15 | ∞ | 0.7795 | 1.50700 | 63.26 |
| 16 (Image pickup surface) | | | | |

| Various data | |
|---|---|
| f | 1.056 |
| Fno. | 3.007 |
| ω | 65.0 |
| IH | 1.000 |
| LTL | 10.35 |

Example 7

| Unit mm | | | | |
|---|---|---|---|---|
| Surface data | | | | |
| Surface no. | r | d | ne | νd |
| Object plane | ∞ | 26.7261 | | |
| 1 | ∞ | 0.4429 | 1.88815 | 40.76 |
| 2 | 1.4150 | 0.8669 | | |
| 3 | −8.7675 | 1.3062 | 1.93429 | 18.90 |
| 4 | −6.4711 | 0.5153 | | |
| 5 | ∞ | 0.8909 | 1.51500 | 75.00 |
| 6 (Stop) | ∞ | 0.0668 | | |
| 7 | ∞ | 0.2607 | | |
| 8 | 10.8391 | 1.6002 | 1.82017 | 46.62 |
| 9 | −2.8953 | 0.2050 | | |
| 10 | 4.0017 | 1.5562 | 1.69979 | 55.53 |
| 11 | −1.8584 | 0.5570 | 1.93429 | 18.90 |
| 12 | −13.4465 | 0.5524 | | |
| 13 | ∞ | 1.0022 | 1.51825 | 64.14 |
| 14 | ∞ | 0.0223 | 1.51500 | 64.00 |
| 15 | ∞ | 0.7795 | 1.50700 | 63.26 |
| 16 (Image pickup surface) | | | | |

| Various data | |
|---|---|
| f | 1.041 |
| Fno. | 3.004 |
| ω | 67.3 |
| IH | 1.000 |
| LTL | 10.62 |

Example 8

| Unit mm | | | | |
|---|---|---|---|---|
| Surface data | | | | |
| Surface no. | r | d | ne | νd |
| Object plane | ∞ | 26.7261 | | |
| 1 | ∞ | 0.4431 | 1.88815 | 40.76 |
| 2 | 1.5524 | 0.8580 | | |
| 3 | −8.0141 | 1.3686 | 1.93429 | 18.90 |
| 4 | −7.1560 | 0.3707 | | |
| 5 | ∞ | 0.8909 | 1.51500 | 75.00 |
| 6 (Stop) | ∞ | 0.0668 | | |
| 7 | ∞ | 0.2565 | | |
| 8 | 7.2803 | 1.8068 | 1.69979 | 55.53 |
| 9 | −2.7024 | 0.2153 | | |

-continued

Unit mm

| | | | | |
|---|---|---|---|---|
| 10 | 4.6344 | 1.6055 | 1.74678 | 49.34 |
| 11 | −1.6553 | 0.5583 | 1.93429 | 18.90 |
| 12 | −7.7057 | 0.5676 | | |
| 13 | ∞ | 1.0022 | 1.51825 | 64.14 |
| 14 | ∞ | 0.0223 | 1.51500 | 64.00 |
| 15 | ∞ | 0.7795 | 1.50700 | 63.26 |
| 16 (Image pickup surface) | | | | |

Various data

| | |
|---|---|
| f | 1.050 |
| Fno. | 3.001 |
| ω | 65.6 |
| IH | 1.000 |
| LTL | 10.81 |

Numerical values of conditional expressions (1) to (9) for the objective optical system for endoscopes according to example 1 to 8 are shown below.

Conditional expression

| | Example1 | Example2 | Example3 | Example4 |
|---|---|---|---|---|
| (1) $f_1/Ih$ | −1.464 | −1.491 | −1.540 | −1.554 |
| (2) $SF_3$ | 0.427 | 0.342 | 0.451 | 0.213 |
| (3) $SF_{34}$ | 0.061 | −0.082 | −0.045 | 0.021 |
| (4) $(1/Fno) \times (f_1/f_5)$ | 0.242 | 0.229 | 0.253 | 0.222 |
| (5) $f_{23}/f_5$ | −1.387 | −1.203 | −1.338 | −1.346 |
| (6) $f_1/f_4$ | −0.756 | −0.797 | −0.747 | −0.713 |
| (7) $R_{1R}/R_{4L}$ | 0.413 | 0.323 | 0.348 | 0.264 |
| (8) $R_{1R}/R_{5R}$ | 0.0000 | −0.1350 | 0.0000 | −0.0620 |
| (9) ω | 66.7 | 65.4 | 66.6 | 81.1 |

| | Example5 | Example6 | Example7 | Example8 |
|---|---|---|---|---|
| (1) $f_1/Ih$ | −1.509 | −1.398 | −1.593 | −1.748 |
| (2) $SF_3$ | 0.449 | 0.427 | 0.578 | 0.459 |
| (3) $SF_{34}$ | −0.140 | 0.062 | −0.160 | −0.263 |
| (4) $(1/Fno) \times (f_1/f_5)$ | 0.172 | 0.229 | 0.224 | 0.247 |
| (5) $f_{23}/f_5$ | −1.169 | −1.376 | −1.122 | −1.166 |
| (6) $f_1/f_4$ | −0.782 | −0.723 | −0.782 | −0.953 |
| (7) $R_{1R}/R_{4L}$ | 0.317 | 0.395 | 0.354 | 0.335 |
| (8) $R_{1R}/R_{5R}$ | −0.1236 | 0.0000 | −0.1052 | −0.2015 |
| (9) ω | 65.9 | 65.0 | 67.3 | 65.6 |

Various embodiments of the present invention have been described above. However, the present invention is not limited to these embodiments, and embodiments in which the arrangements of these embodiments are combined without departing from the scope of the invention are also in the category of the present invention.

As described above, the present invention is useful for a small-sized and bright objective optical system for endoscope having a wide angle of view, which achieves a highly-defined image.

According to the present invention, an effect is shown that it is possible to provide a small-sized and bright objective optical system for endoscope having a small number of lenses and a wide angle of view to deal with further thinning of a diameter and larger number of pixels of an endoscope.

What is claimed is:

1. An objective optical system for an endoscope, the objective optical system consisting of, in order from an object side:
a front lens group having a negative refractive power as a whole;
an aperture stop; and
a rear lens group having a positive refractive power as a whole,
wherein:
the front lens group consists of, as lenses having a refractive power, in order from the object side, a first lens which is a single lens having a negative refractive power and a second lens which is a single lens having a positive refractive power,
the rear lens group includes a third lens which is a single lens having a positive refractive power, and a cemented lens of a fourth lens having a positive refractive power and a fifth lens having a negative refractive power,
an object-side surface of the first lens is a flat surface,
the second lens has a meniscus shape having a convex surface directed toward an image side,
the third lens has a biconvex shape, and
the objective optical system for endoscope satisfies the following conditional expressions (1) and (2)

$$-2.0 \leq f_1/Ih \leq -1.39 \quad (1)$$

$$-0.2 \leq SF_3 \leq 0.61 \quad (2)$$

where,
$f_1$ denotes a focal length of the first lens,
Ih denotes the maximum image height of the objective optical system for endoscope, and
$SF_3$ denotes a shape factor which is expressed by $SF_3 = (R_{3L}+R_{3R})/(R_{3L}-R_{3R})$, when a radius of curvature of an object-side surface of the third lens is let to be $R_{3L}$ and a radius of curvature of an image-side surface of the third lens is lens to be $R_{3R}$.

2. The objective optical system for endoscope according to claim 1, wherein the objective optical system satisfies the following conditional expression (3)

$$-0.27 \leq SF_{34} \leq 0.37 \quad (3)$$

where,
$SF_{34}$ denotes a shape factor which is expressed by $SF_{34} = (R_{3R}+R_{4L})/(R_{3R}-R_{4L})$, when a radius of curvature of an image-side surface of the third lens is let to be $R_{3R}$ and a radius of curvature of an object-side surface of the fourth lens is let to be $R_{4L}$.

3. The objective optical system for endoscope according to claim 1, wherein the objective optical system satisfies the following conditional expression (4)

$$0.15 \leq (1/Fno) \times (f_1/f_5) \leq 0.3 \quad (4)$$

where,
Fno denotes an effective F-number of the objective optical system for endoscope,
$f_1$ denotes the focal length of the first lens, and
$f_5$ denotes the focal length of the fifth lens.

4. The objective optical system for endoscope according to claim 1, wherein the second lens and the third lens are arranged in this order from the object side to the image side with a fixed spacing therebetween and with no intervening refractive optical elements therebetween, and
wherein the objective optical system satisfies the following conditional expression (5)

$$-2.0 \leq f_{23}/f_5 \leq -1.0 \quad (5)$$

where,
$f_{23}$ denotes a combined focal length of the second lens and the third lens, and
$f_5$ denotes a focal length of the fifth lens.

5. The objective optical system for endoscope according to claim 1, wherein the objective optical system for endoscope satisfies the following conditional expression (6)

$$-1.1 \leq f_1/f_4 \leq -0.7 \quad (6)$$

where, $f_1$ denotes the focal length of the first lens, and
$f_4$ denotes the focal length of the fourth lens.

6. The objective optical system for endoscope according to claim 1, wherein the objective optical system for endoscope satisfies the following conditional expression (7)

$$0.25 \leq R_{1R}/R_{4L} \leq 0.7 \quad (7)$$

where, $R_{1R}$ denotes a radius of curvature of an image-side surface of the first lens, and
$R_{4L}$ denotes a radius of curvature of an object-side surface of the fourth lens.

7. The objective optical system for endoscope according to claim 1, wherein the objective optical system for endoscope satisfies the following conditional expression (8)

$$-0.3 \leq R_{1R}/R_{5R} \leq 0 \quad (8)$$

where, $R_{1R}$ denotes a radius of curvature of an image-side surface of the first lens, and
$R_{5R}$ denotes a radius of curvature of an image-side surface of the fifth lens.

8. The objective optical system for endoscope according to claim 1, wherein the objective optical system for endoscope satisfies the following conditional expression (9)

$$\omega \geq 62° \quad (9)$$

where, $\omega$ denotes a half angle of view of the objective optical system for endoscope.

* * * * *